United States Patent
Park et al.

(10) Patent No.: US 6,740,263 B2
(45) Date of Patent: May 25, 2004

(54) ANTHRACENE COMPOUND AND CHEMILUMINESCENT COMPOSITION COMPRISING THE SAME

(75) Inventors: Koon Ha Park, Daejeon (KR); Yong Fan Kim, Gongju (KR); Min Seob Park, Cheonan (KR)

(73) Assignee: Myung-Sook Yeom (KR)

( * ) Notice: Subject to any disclaimer, the term of this patent is extended or adjusted under 35 U.S.C. 154(b) by 149 days.

(21) Appl. No.: 10/071,958

(22) Filed: Feb. 7, 2002

(65) Prior Publication Data

US 2003/0116759 A1 Jun. 26, 2003

(30) Foreign Application Priority Data

Oct. 22, 2001 (KR) ........................ 2001-65155

(51) Int. Cl.[7] .............................. C09K 3/00; C07C 19/08
(52) U.S. Cl. .................... 252/700; 585/26; 585/425; 570/129; 570/183
(58) Field of Search .................... 252/700; 585/26, 585/425; 570/129, 183

(56) References Cited

U.S. PATENT DOCUMENTS

| 3,749,679 A | | 7/1973 | Rauhut |
| 3,816,326 A | | 6/1974 | Bollyky |
| 3,944,820 A | | 3/1976 | Stotts |
| 3,974,368 A | | 8/1976 | Rauhut |
| 4,379,320 A | | 4/1983 | Mohan et al. |
| 4,462,931 A | | 7/1984 | Cohen et al. |
| 4,678,608 A | | 7/1987 | Dugliss |
| 4,717,511 A | | 1/1988 | Koroscil |
| 4,751,616 A | | 6/1988 | Smithey |
| 4,845,223 A | | 7/1989 | Seybold et al. |
| 5,122,306 A | | 6/1992 | Van Moer et al. |
| 5,232,635 A | * | 8/1993 | Van Moer et al. ........... 252/700 |
| 6,566,572 B2 | * | 5/2003 | Okamoto et al. ........... 585/469 |

OTHER PUBLICATIONS

Workentin et al, Remote substituent Effects on the Reactivity of 9–Aryl and 9,10–Diarylanthracene Radical cations with anions and Amines, J. Phys. Chem. A, vol. 102, No. 32, pp. 6503–6512, 1998.*

Antonkina et al., Electrochemical Behavior of Polycyclic arenes– Activators of Peroxide–Oxalate Chemiluminescence, Elektrokhimiya, vol. 27, No. 3, pp. 380–387, 1991.*

* cited by examiner

Primary Examiner—Philip C. Tucker
(74) Attorney, Agent, or Firm—Cantor Colburn LLP

(57) ABSTRACT

The present invention discloses an anthracene compound represented by the following formula 4 and chemiluminescent composition comprising the compound:

[Formula 4]

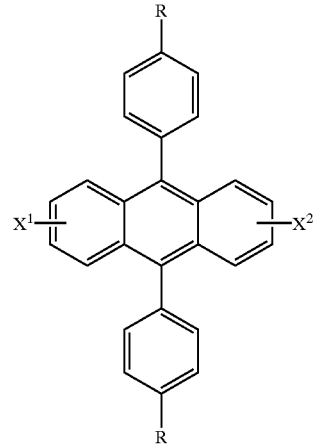

wherein R is an alkyl group having 1–8 carbon atoms, and $X^1$ and $X^2$ are independently hydrogen or halogen.

16 Claims, No Drawings

ANTHRACENE COMPOUND AND CHEMILUMINESCENT COMPOSITION COMPRISING THE SAME

BACKGROUND OF THE INVENTION

1. Field of the Invention

The present invention relates to an anthracene compound and a chemiluminescent composition comprising the compound, and more particularly to a novel anthracene compound which is capable of emitting a blue light of a high intensity for a prolonged period of time compared with conventional anthracene compounds used as luminescent dyes in chemiluminescent compositions emitting blue light, and a chemiluminescent composition comprising the novel compound.

2. Description of the Related Art

One example of known chemiluminescent solutions includes a mixed solution of a chemiluminescent oxalate composition comprising a luminous dye and a solution containing peroxide.

The chemiluminescent oxalate composition generally contains a luminescent dye, an oxalate and a solvent. The peroxide-containing solution contains peroxide, a catalyst and a solvent.

The color of light generated from the chemiluminescent solution is determined by the luminescent dye used in the chemiluminescent oxalate composition. As the luminescent dye emitting a blue light, an anthracene compound is known.

As the anthracene compound emitting a blue light, a 9,10-diphenylanthracene compound described in the following formula 1 and a luminescent composition comprising the compound is known.

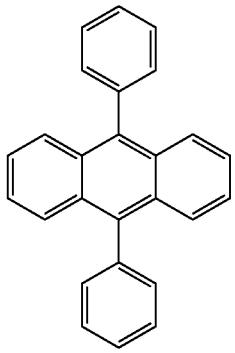

[Formula 1]

However, there is a disadvantage that the intensity and color of light emitted from the chemiluminescent solution comprising the 9,10-diphenylanthracene compound are rendered unstable with the lapse of time.

Therefore, there have been continuous attempts to find a luminescent dye that stably emits clear blue light. In particular, due to the fact that the physical properties of the 9,10-diphenylanthracene compound change with a substituent applied to the compound, many studies have been investigated.

As one of such studies, U.S. Pat. No. 4,678,608 discloses a chemiluminescent composition using a 9,10-bis(4-methylphenyl)anthracene compound represented by the following formula 2.

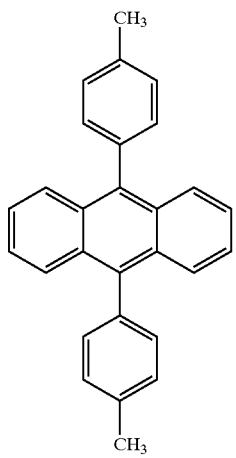

[Formula 2]

However, where the 9,10-bis(4-methylphenyl)anthracene compound is used in the chemiluminescent oxalate composition, it loses a desired stability. For this reason, the compound cannot be used in products requiring that luminescence be maintained for 5 hours or more.

Also, U.S. Pat. No. 4,717,511 discloses a chemiluminescent composition using 9,10-bis(4-methoxyphenyl)-2-chloroanthracene described in the following formula 3

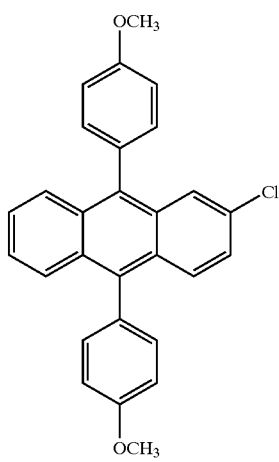

[Formula 3]

However, there is a disadvantage that the 9,10-bis(4-methoxyphenyl)-2-chloroanthracene compound emits pale blue light.

Therefore, the present inventor has endeavored to develop a compound that is capable of emitting a clear blue light for a prolonged period of time, and the present invention has been accomplished by such studies.

SUMMARY OF THE INVENTION

Therefore, the present invention has been made in view of the above problems, and it is an object of the present invention to provide an anthracene compound which has excellent stability over the conventional luminescent dye emitting blue light, thereby emitting a chemiluminescent light of clear deep blue.

It is another object of the present invention to provide a chemiluminescent composition and a chemiluminescent solution using the anthracene compound.

In accordance with one aspect of the present invention, there is provided an anthracene compound represented by the following formula(4):

[Formula 4]

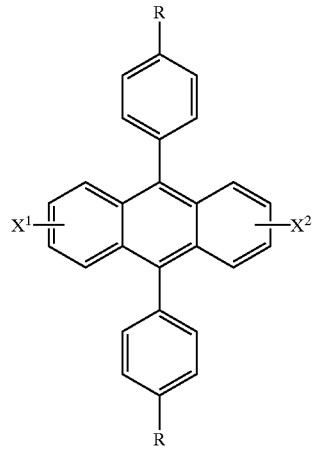

wherein R is a alkyl group having 1–8 carbon atoms, $X^1$ and $X^2$ are independently hydrogen or halogen.

In accordance with another aspect of the present invention, there is provided a preparation method of an anthracene compound comprising:

refluxing a compound of the following formula(11) with magnesium metal in an organic solvent and cooling the refluxed solution, thereby affording a compound of the following formula(12);

mixing the obtained compound of the formula(12) and anthraquinone of the following formula(13) in an organic solvent, refluxing the resulting solution adding an aqueous acidic solution, for example, 10% hydrochloric acid solution, extracting an organic phase, and distilling the extracted organic solvent under a vacuum, thereby producing a brown solution of the following formula(14); and adding acetic acid and a catalyst to the obtained brown solution, and refluxing the resulting solution, thereby obtaining the solid compound of the formula(4).

[Formula 11]

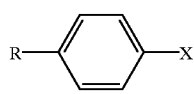

wherein R is an alkyl group having 1–8 carbon atoms, and X is halogen.

[Formula 12]

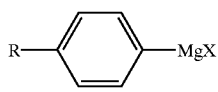

wherein R is an alkyl group having 1–8 carbon atoms, and X is halogen.

[Formula 13]

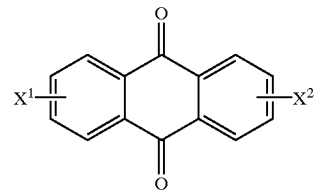

wherein $X^1$ and $X^2$ are independently hydrogen or halogen.

[Formula 14]

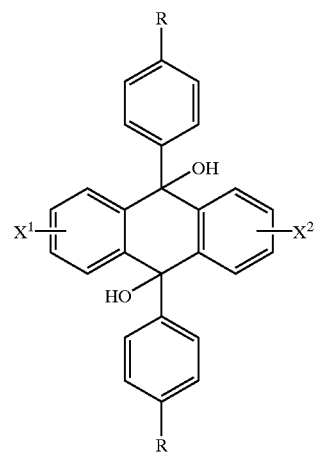

wherein R is an alkyl group having 1–8 carbon atoms, and $X^1$ and $X^2$ are independently hydrogen or halogen.

[Formula 4]

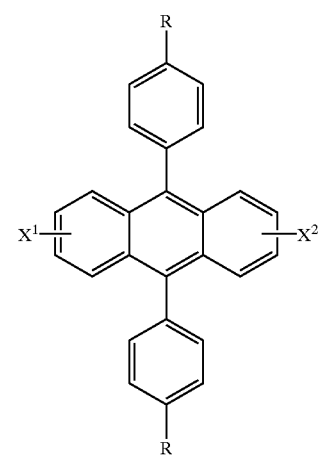

wherein R is an alkyl group having 1–8 carbon atoms, and $X^1$ and $X^2$ are independently hydrogen or halogen.

In accordance with another aspect of the present invention, there is provided a chemiluminescent composition containing the anthracene compound represented by the following formula(4):

[Formula 4]

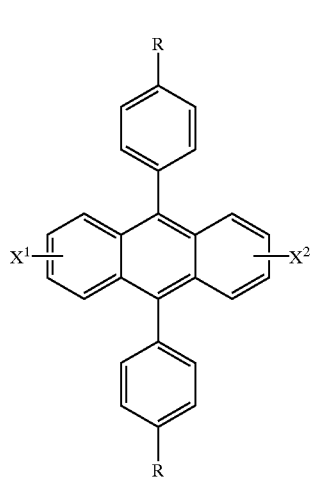

wherein R is a alkyl group having 1–8 carbon atoms, $X^1$ and $X^2$ are independently hydrogen or halogen, the chemiluminescent composition emitting chemiluminescent light by reaction with peroxide.

DESCRIPTION OF THE PREFERRED EMBODIMENTS

The present invention can be achieved by providing an anthracene compound represented by the following formula 4:

[Formula 4]

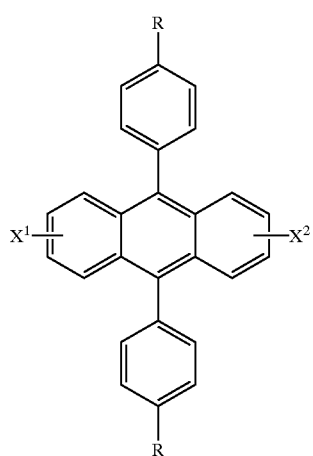

wherein R is a alkyl group having 1–8 carbon atoms, and $X^1$ and $X^2$ are independently hydrogen or halogen.

A more preferred compound of the formula 4 is an anthracene compound represented by the following formula 5, in which $X^1$ is hydrogen and $X^2$ is halogen:

[Formula 5]

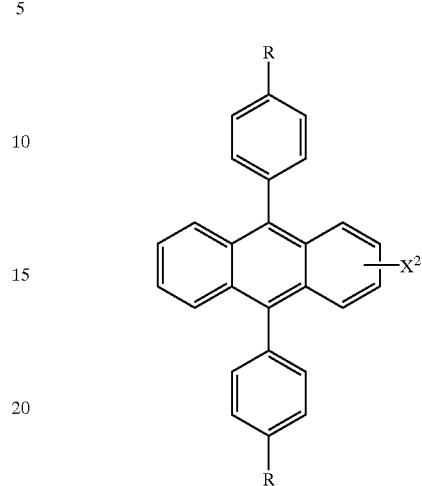

wherein R is a alkyl group having 1–8 carbon atoms, and $X^2$ is halogen.

A more preferred compound of the formula 5 is an anthracene compound represented by the following formula 6, in which $X^2$ is Cl:

[Formula 6]

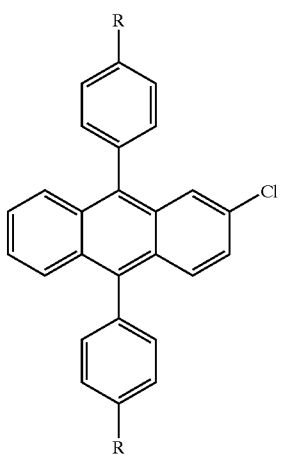

wherein R is a alkyl group having 1–8 carbon atoms.

A more preferred compound of the formula 6 is 9,10-bis(4-methylphenyl)-2-chloroanthracene of the following formula 7, wherein R is a methyl group; 9,10-bis(4-ethylphenyl)-2-chloroanthracene of the following formula 8, wherein R is a ethyl group; 9,10-bis(4-propylphenyl)-2-chloroanthracene of the following formula 9, wherein R is a propyl group; or 9,10-bis(4-t-butylphenyl)-2-chloroanthracene of the following formula 10, wherein R is a t-butyl group:

[Formula 7]

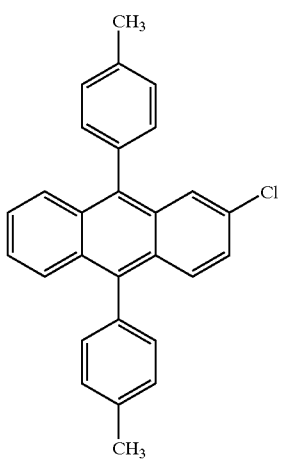

[Formula 8]

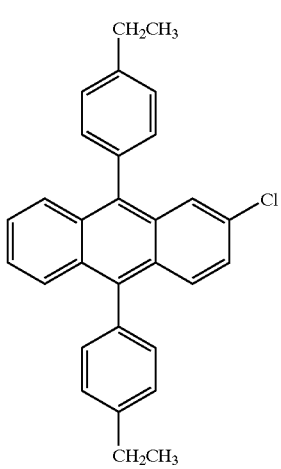

[Formula 9]

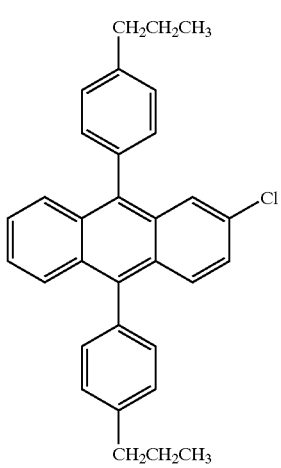

[Formula 10]

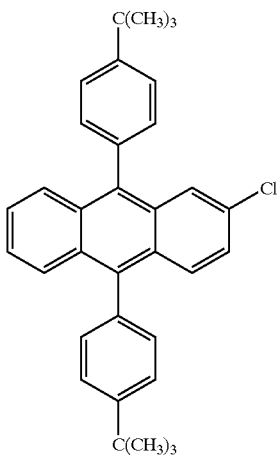

To prepare effectively the anthracene compound of the formula 4, the present invention provides a preparation method comprising the steps of:

refluxing a compound of the following formula 11 with magnesium metal in an organic solvent for 3 hours or more, and cooling the refluxed solution, thereby obtaining a compound of the following formula 12;

stirring the obtained compound of the formula 12 and anthraquinone of the following formula 13 in an organic solvent for 3 hours or more, refluxing the resulting solution for 3 hours or more, stirring the resulting solution after adding an aqueous 10% hydrochloric acid solution, extracting only the organic solvent, and distilling the extracted organic solvent under a vacuum, thereby obtaining a brown solution of the following formula 14; and adding acetic acid and a catalyst to the obtained brown solution, stirring the mixed solution for 1 hour or more, refluxing the stirred solution for 3 hours or more, stirring again the refluxed solution for 3 hours or more, and treating the resulting solution using a recrystallization method, thereby obtaining the solid compound of the formula 4.

[Formula 11]

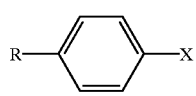

wherein R is an alkyl group having 1–8 carbon atoms, and X is halogen.

[Formula 12]

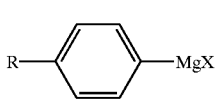

wherein R is an alkyl group having 1–8 carbon atoms, and X is halogen.

[Formula 13]

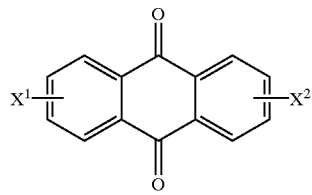

wherein $X^1$ and $X^2$ is independently hydrogen or halogen.

[Formula 14]

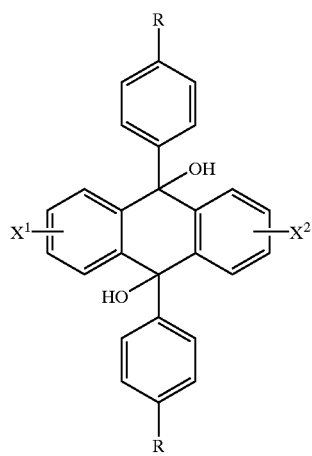

wherein R is an alkyl group having 1–8 carbon atoms, $X^1$ and $X^2$ is independently hydrogen or halogen.

As described above, the compound of the formula 11 is refluxed with magnesium metal in the organic solvent for 3 hours or more. The refluxed solution is cooled. In this way, the compound of the formula 12 is obtained.

Various organic solvents can be used in this step. Anhydrous tetrahydrofuran is used as a preferred organic solvent in the present invention. The compound of the formula 11 and magnesium metal are added to the anhydrous tetrahydrofuran solvent at a same equivalent. The resulting solution is refluxed for 3 hours or more and then cooled.

The compound of the formula 11 may be selected from compounds having the structure of the formula 11, wherein X is halogen, and R is an alkyl group having 1–8 carbon atoms, and preferably, wherein X is halogen, and R is methyl, ethyl, propyl or t-butyl group.

The compound of the formula 12 obtained from the above step and anthraquinone of the formula 13 are stirred in the organic solvent for 3 hours or more. The stirred solution is refluxed for 3 hours or more, and stirred after being added with an aqueous 10% hydrochloric acid solution. An organic solvent is extracted, and the extracted solution is distilled under a vacuum. In this way, the brown solution of the formula 14 is obtained.

A more preferred compound of the formula 13 is an anthracene compound represented by the following formula 15, in which $X^1$ is hydrogen, and $X^2$ is halogen:

[Formula 15]

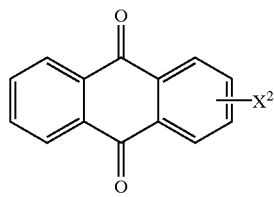

wherein $X^2$ is halogen(F, Cl or Br).

A particularly preferred compound of the formula 15 is an anthracene compound represented by the following formula 16, in which $X^1$ is hydrogen, and $X^2$ is halogen:

[Formula 16]

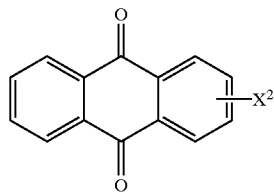

The compound of the formula 12 and anthraquinone of the formula 13 are added to tetrahydrofuran at the same equivalent. The mixed solution is stirred for 3 hours or more, refluxed for 3 hours or more. An aqueous 10% hydrochloric acid solution is added to the refluxed solution, and stirred. An organic solvent is extracted, and the extracted organic solvent is distilled under a vacuum, by which the brown solution of the formula 14 is obtained.

Glacial acetic acid and a reducing agent are added to the brown solution. The mixed solution was stirred at room temperature for 1 hour or more, and refluxed for 3 hours or more. The refluxed solution is stirred again for 1 hour or more, by which the compound of the formula 4 was obtained using a recrystallization method in glacial acetic acid.

Various kinds of reducing agents can be selected and used as a catalyst, and $SnCl_2$ is used preferably as the reducing agent according to the invention.

As described above, glacial acetic acid and a reducing agent are added to the brown solution of the formula 14. The mixed solution is stirred at room temperature for 1 hour or more, refluxed for 3 hours or more, and stirred again at room temperature for 1 hour or more. The resulting solution is subject to a conventional recrystallization method, by which the anthracene compound of the formula 4 is obtained in the form of solid.

The anthracene compound represented by the above The formula 4 emits light of blue series having wavelengths of 400 nm to 500 nm under prescribed conditions for obtaining chemiluminescence using conventional anthracene compounds. The anthracene compound can also generate variously colored light by proper mixing with other fluorescent dyes. Accordingly, the anthracene compound of the formula 4 according to the invention can be used as a fluorescent dye in compositions for emitting chemiluminescence light, similar to the conventional anthracene compounds.

Accordingly, the present invention provides a chemiluminescent composition comprising the anthracene compound of the formula 4, capable of generating chemiluminescence by reaction with peroxide.

Preferably, the anthracene compound of the formula 4 is present in the composition according to the present invention in an amount of 0.1 to 1.0 parts by weight, based on 100 parts by weight of the composition. Where the anthracene compound is present in an amount of less than 0.1% by weight, there is a problem that the generated light is poor in intensity and duration. Where the anthracene compound is present in an amount of more than 1.0%, the anthracene compound may be precipitated in the form of solid. Accordingly, it is preferable that the anthracene compound is contained in the prescribed range. More preferably, the anthracene compound is present in the composition in an amount of, 0.15 to 0.5 parts by weight, based on 100 parts by weight of the composition.

More preferably, the anthracene compound of the formula 4 is selected from the group consisting of 9,10-bis(4-methylphenyl)-2-chloroanthracene, 9,10-bis(4-ethylphenyl)-2chloroanthracene, 9,10-bis(4-propylphenyl)-2-chloroanthracene and 9,10-bis(4-t-butylphenyl)-2-chloroanthracene.

The chemiluminescent composition comprising the anthracene compound of the formula 4 also comprises a solvent. According to the present invention, the solvent may be selected from the group consisting of tertiary alcohols, dibutyl phthalate, butyl benzoate and the mixtures thereof.

The chemiluminescent composition according to the present invention also contains an oxalate compound. Preferably, bis(2,4,5-trichloro-6-carbopentoxyphenyl) oxalate may be used as the oxalate compound.

According to the invention, the oxalate compound is present in the composition in an amount of 5 to 18 parts by weight, based on 100 parts by weight of the composition. Where the oxalate compound is present in an amount of less than 5.0 parts by weight, based on 100 parts by weight of the composition, the intensity of light will be very weak. Where the oxalate compound present in an amount of more than 18%, there will be a problem in that the oxalate compound is precipitated in the form of solid. Accordingly, it is preferable that the oxalate compound is contained in the prescribed range. More preferably, the oxalate compound is present in the composition in an amount of 9.0 to 15.0 parts by weight, based on 100 parts by weight of the composition.

The chemiluminescent composition according to the present invention may generate chemiluminescence by reaction with peroxide. As described above, the chemiluminescent composition comprising anthracene of the formula 4 emits blue light of 400 to 500 nm by reaction with peroxide.

In this regard, the present invention provides a chemiluminescent solution containing the chemiluminescent composition and a solution containing peroxide.

Preferably, the chemiluminescent composition and the peroxide-containing solution are mixed in a ratio of 1:1 to 5:1. Where the ratio of the chemiluminescent composition to the peroxide-containing solution is less than 1:1, the duration of chemiluminescence will be shorter. Where the ratio of the chemiluminescent composition to the peroxide-containing solution is more than 5:1, the initial chemiluminescence is weak. Accordingly, it is preferable that the chemiluminescent composition and the solution containing peroxide are mixed in the prescribed range. More preferably, the chemiluminescent composition and the peroxide-containing solution are mixed in a ratio of 2.5:1 to 3.5:1.

It is preferable that the peroxide-containing solution contains peroxide in an amount of 0.5 to 5 parts by weight, based on 100 parts by weight of the solution. Where peroxide is present in the solution in an amount of less than 0.5 parts by weight, based on 100 parts by weight of the solution, the initial chemiluminescence will be weak. Where peroxide is present in an amount of more than 5%, the intensity of initial chemiluminescent light is so high that the duration of chemiluminescence is shorter. Accordingly, it is preferable that peroxide is present in the prescribed range. The peroxide-containing solution more preferably contains peroxide in an amount of 1 to 3 parts by weight, based on 100 parts by weight of the solution. Peroxide may be hydrogen peroxide or peroxides of carboxylic acid and the like, but is preferably hydrogen peroxide in view of reactivity.

The peroxide-containing solution also contains a solvent. According to the present invention, the solvent is selected from the group consisting of tertiary alcohol, dimethyl phthalate, dibutyl phthalate, butyl benzoate and the mixtures thereof.

Further, the peroxide-containing solution contains a catalyst. In the present invention, salicylate is preferably used as the catalyst. The catalyst is preferably present in the solution in an amount of 0.003 to 0.03 parts by weight, based on 100 parts by weight of the solution.

When the peroxide-containing solution having the above composition is mixed with the chemiluminescent composition of the present invention in the prescribed ratio, deep blue chemiluminescence lasts for 5 to 48 hours or more, and afterglow lasts for 60 hours or more.

The chemiluminescent light generated by the present composition can be used in common application fields, for example, for signaling, decoration, games, hunting, fishing or military purposes.

Now, examples of the present invention will be described in more detail. The following examples are described only for a better understanding of the present invention, and are not intended to limit the invention.

SYNTHETIC EXAMPLE 1

Synthesis of 9,10-bis(4-methylphenyl)-2-chloroanthracene 213.8 g of 4-bromotoluene dissolved in anhydrous THF (200 ml) was slowly added to 32.6 g of magnesium in 500 ml of anhydrous THF for 2 hours. The mixed solution was refluxed for 3 hours, and then cooled to room temperature. 121 g of 2-chloroanthraquinone was added to cooled solution. The resulting solution was stirred for 3 hours, and then refluxed for 3 hours. Then, 400 ml of 10% aqueous hydrochloric acid solution was added to the resulting solution. An organic layer was separated from the solution. The resulting solvent was distilled under a vacuum, by which a brown solution was obtained. 500 ml of Glacial acetic acid and 100 g of $SnCl_2.2H_2O$ were added to the brown solution. The mixed solution was stirred at room temperature for 1 hour, heated for 3 hours and refluxed. The solution was further stirred at room temperature for 3 hours. Thus, a pale yellow product was obtained. This product was recrystallized using glacial acetic acid. In this way, a pure product was obtained in the form of pale yellow crystals(153 g, m.p. 202–203.5° C., yield 78%). Results of $^1H$ NMR(200 MHz, $CDCl_3$) and IR(KBr) for the obtained compound are described in the following Table 1.

SYNTHETIC EXAMPLE 2

Synthesis of 9,10-bis(4-ethylphenyl)-2-chloroanthracene

The procedure of Synthetic Example 1 was repeated using 231 g of p-bromoethylbenzene instead of p-bromotoluene. In this way, a product was obtained in the form of pale yellow crystals(160 g, m.p. 214.5–216.3° C., yield 76%).

Results of $^1$H NMR(200 MHz, CDCl$_3$) and IR(KBr) for the obtained compound are described in the following Table 1.

SYNTHETIC EXAMPLE 3

Synthesis of 9,10-bis(4-propylphenyl)-2-chloroanthracene

The procedure of Synthetic Example 1 was repeated using 249 g of p-bromopropylbenzene instead of p-bromotoluene. In this way, a product was obtained in the form of pale yellow crystals(175 g, m.p. 225–227° C., yield 78%). Results of $^1$H NMR(200 MHz, CDCl$_3$) and IR(KBr) for the obtained compound are described in the following Table 1.

SYNTHETIC EXAMPLE 4

Synthesis of 9,10-bis(4-butylphenyl)-2-chloroanthracene

The procedure of Synthetic Example 1 was repeated using p-bromo-t-butylbenzene(266.4 g) instead of p-bromotoluene. In this way, a product was obtained in the form of pale yellow crystals(190.8 g, dec>350° C., yield 80%). Results of $^1$H NMR(200 MHz, CDCl$_3$) and IR(KBr) for the obtained compound are summarized in the following Table 1.

TABLE 1

| Examples | $^1$H NMR(200 MHz, CDCl$_3$) | IR(cm$^{-1}$) |
|---|---|---|
| Syn. Ex. 1 | δ2.53(s, 6H), δ7.2–7.8(m, 15 H) | 2916, 1602, 1513, 1441, 1392 |
| Syn. Ex. 2 | δ1.40(t, 6 H), δ2.82(q, 4 H), δ7.2–7.8(m, 15 H) | 2962, 1601, 1513, 1439, 1391 |
| Syn. Ex. 3 | δ1.42(t, 6 H), δ1.70(m, 4 H), δ2.85(t, 4 H), δ7.2–7.8(m, 15 H) | 2963, 1602, 1513, 1440, 1391 |
| Syn. Ex. 4 | δ3.91(s, 18 H), δ7.2–7.8(m, 15 H) | 2957, 1602, 1441, 1390 |

Based on Table 1, it is seen that the anthracene compounds obtained from Synthetic Examples 1, 2, 3 and 4 are 9,10-bis(4-methylphenyl)-2-chloroanthracene, 9,10-bis(4-ethylphenyl)-2-chloroanthracene, 9,10-bis(4-propylphenyl)-2-chloroanthracene and 9,10-bis(4-t-butylphenyl)-2-chloroanthracene respectively.

Preparation Example 1 of Chemiluminescent Composition 13.5 g of bis(2,4,5-trichloro-6-carbopentoxyphenyl)oxalate was added to a vessel containing 86.25 g of dibutyl phthalate. The mixed solution was heated to 120° C. and cooled to 60° C. under nitrogen atmosphere while being stirred. Then, 0.250 g of 9,10-bis(4-methylphenyl)-2-chloroanthracene obtained from the Synthetic Example 1 was added the solution. The resulting solution was stirred thoroughly, and then cooled to room temperature, by which a chemiluminescent composition was obtained.

Preparation Example 2 of Chemiluminescent Composition

The procedure of Preparation Example 1 was repeated using an equivalent molar amount of 9,10-bis(4-ethylphenyl)-2-chloroanthracene(0.268 g) obtained from Synthetic Example 2 instead of 9,10-bis(4-methylphenyl)-2-chloroanthracene obtained by Synthetic Example 1, by which a chemiluminescent composition was obtained.

Preparation Example 3 of Chemiluminescent Composition

The procedure of Preparation Example 1 was repeated using an equivalent molar amount of 9,10-bis(4-propylphenyl)-2-chloroanthracene(0.286 g) obtained from Synthetic Example 3 instead of 9,10-bis(4-methylphenyl)-2-chloroanthracene obtained by Synthetic Example 1, by which a chemiluminescent composition was obtained.

Preparation Example 4 of Chemiluminescent Composition

The procedure of Preparation Example 1 was repeated using an equivalent molar amount of 9,10-bis(4-t-butylphenyl)-2-chloroanthracene(0.10 g) obtained from Synthetic Example 4 instead of 9,10-bis(4-methylphenyl)-2-chloroanthracene obtained by Synthetic Example 1 due to solubility, by which a chemiluminescent composition was obtained.

Comparative Preparation Example 1 of Chemiluminescent Composition

The procedure of Preparation Example 1 was repeated using an equivalent molar amount of known 9,10-bis(4-methoxyphenyl)-2-chloroanthracene(0.270 g) instead of 9,10-bis(4-methylphenyl)-2-chloroanthracene obtained by Synthetic Example 1, by which a chemiluminescent composition was obtained.

Comparative Preparation Example 2 of Chemiluminescent Composition

The procedure of Preparation Example 1 was repeated using equivalent molar amounts of known 9,10-bis(4-methylphenyl)anthracene(0.228 g) instead of 9,10-bis(4-methylphenyl)-2-chloroanthracene obtained by Synthetic Example 1, by which a chemiluminescent composition was obtained.

Preparation Example 1 to 4 of Chemiluminescent Solution 4.0 g of Hydrogen peroxide and 0.018 g of salicylate were added to 96 g of a mixed solution of dimethyl phthalate and t-butanol(8:2). The obtained solution was mixed with each of the compositions obtained from Preparation Examples 1 to 4 in the ratio of 1:3 to a total weight of 4.0 g, by which chemiluminescent solutions were obtained. Then, the intensity of light was measured at intervals by a powermeter(from Coherent Co.; Model No.: FM) while all outside light was excluded in a box of 28 cm×25 cm×13 cm in size. The results are summarized in the following Table 2.

TABLE 2

| | Light intensity (nW) according to time (hr) | | | | | | | | | | |
|---|---|---|---|---|---|---|---|---|---|---|---|
| Examples | 0.5 | 1 | 2 | 3 | 4 | 6 | 8 | 10 | 12 | 24 | Av. |
| Ex. 1 | 230 | 148 | 84 | 65 | 41 | 25 | 14 | 13 | 9 | 4 | 57.63 |
| Ex. 2 | 240 | 154 | 96 | 75 | 50 | 30 | 19 | 15 | 9 | 5 | 63.18 |
| Ex. 3 | 249 | 159 | 106 | 84 | 62 | 38 | 25 | 18 | 12 | 7 | 69.36 |
| Ex. 4 | 197 | 132 | 76 | 54 | 37 | 21 | 11 | 9 | 7 | 4 | 50.18 |
| Com. Ex. 1 | 257 | 148 | 87 | 62 | 35 | 19 | 10 | 6 | 4 | 0 | 57.18 |
| Com. Ex. 2 | 130 | 65 | 35 | 25 | 16 | 15 | 9 | 5 | 3 | 0 | 27.72 |

As shown in Table 2, it was found that 1 hour after initial light emission, chemiluminescent solutions of Examples 1 to 4 according to the present invention emitted a light of high intensity for a prolonged period of time, as compared with Comparative Examples 1 and 2. Also, chemiluminescent solutions of Examples 1 to 4 exhibit superior afterglow characteristics over Comparative Examples 1 and 2. Although results of 24 hours later are not shown in Table 2, afterglow could be macroscopically observed from Examples 1 to 4, the chemiluminescent solutions according to the present invention, even after 48 hours.

As described above, the present invention provides a chemiluminescent composition, which has excellent stability compared with conventional chemiluminescent compositions generating blue light, and which has strong initial light intensity and long afterglow duration. The present invention also provides a chemiluminescent solution based on the chemiluminescent composition.

What is claimed is:

1. An anthracene compound, represented by the following formula (5):

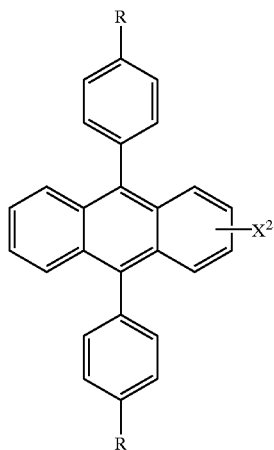

[Formula 5]

wherein R is an alkyl group having 1–8 carbon atoms, and $X^2$ is halogen.

2. The anthracene compound as set form in claim 1, represented by the following formula (6) corresponding to the formula (5), wherein $X^2$ is Cl:

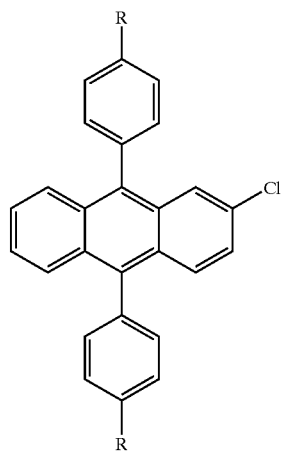

[Formula 6]

wherein R is an alkyl group having 1–8 carbon atoms.

3. The anthracene compound as set forth in claim 2, wherein the formula (6) is 9,10-bis(4-methylphenyl)-2-chloroanthracene, 9,10-bis(4-ethylphenyl)-2-chloroanthracen 9,10-bis(4propylphenyl)-2-chloroanthracene or 9,10-bis(4-t-butylphenyl)-2-chloroanthracene, wherein R has 1–4carbon atoms, respectively.

4. A preparation method of an anthracene compound comprising:
refluxing a compound of the following formula (11) with magnesium metal in an organic solvent and cooling the refluxed solution, thereby obtaining a compound of the following formula (12);
mixing the obtained compound of the formula (12) and anthraquinone of the following formula (13) in an organic solvent, refluxing the resulting solution, adding an aqueous acid solution to the resulting solution, extracting an organic phase, and distilling the extracted organic phase, thereby obtaining a brown solution of the following formula (14); and
reacting acetic acid and a catalyst with the brown solution, thereby obtaining a compound of the formula (5)

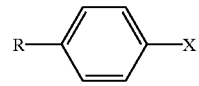

[Formula 11]

wherein R is an alkyl group having 1–8 carbon atoms, and X is halogen;

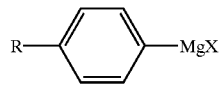

[Formula 12]

wherein R is an alkyl group having 1–8 carbon atoms, and X is halogen;

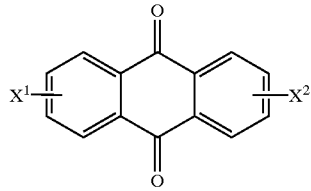

[Formula 13]

wherein $X^1$ is hydrogen and $X^2$ is halogen;

[Formula 14]

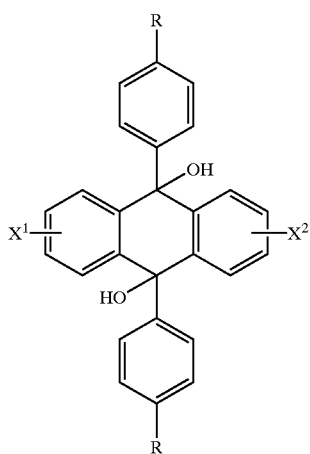

wherein R is an alkyl group having 1–8 carbon atoms, and $X^1$ is hydrogen and $X^2$ is halogen;

[Formula 5]

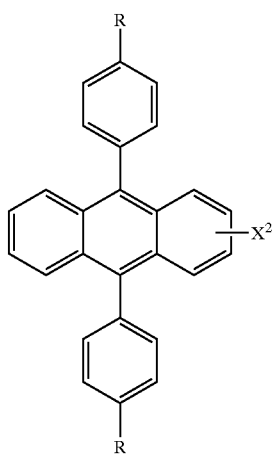

wherein R is an alkyl group having 1–8 carbon atoms, and $X^2$ is halogen.

5. The preparation method as set forth in claim 4, wherein the aqueous acid solution is an aqueous hydrochloric acid solution.

6. The preparation method as set forth in claim 4, further comprising recrystallizing a resultant of the reaction of the acetic acid and the brown solution.

7. A chemiluminescent composition containing the anthracene compound of claim 1.

8. The chemiluminescent composition as set forth in claim 7, wherein the anthracene compound is selected from the group consisting of 9,10-bis(4-methylphenyl)-2chloroanthracene, 9,10-bis(4-ethylphenyl)-2-chloroanthracene, 9,10-bis(4-propylphenyl)-2-chloroanthracene and 9,10-bis(4-t-butylphenyl)-2-chloroanthracene.

9. The chemiluminescent composition as set forth in claim 9, further comprising a solvent.

10. The chemiluminescent composition as set forth in claim 9, wherein the solvent is selected from the group consisting tertiary alcohols, dibutyl phthalate, butyl benzoate, dimethyl phthalate and mixtures comprising at least one of the foregoing.

11. The chemiluminescent composition as set forth in claim 7, further comprising an oxalate compound.

12. The chemiluminescent composition as set forth in claim 11, wherein the oxalate compound is bis(2,4,5-trichloro-6-carbopentoxyphenyl)oxalate.

13. A chemiluminescent composition as set forth in claim 7, further comprising a peroxide-containing component.

14. The chemiluminescent composition as set forth in claim 13, wherein the peroxide-containing component contains a solvent selected from the group consisting of tertiary alcohols, dibutyl phthalate, butyl benzoate, dimethyl phthalate and mixtures comprising at least one of the foregoing.

15. The chemiluminescent composition as set forth in claim 14, wherein the peroxide-containing component further contains a catalyst.

16. The chemiluminescent composition as set forth in claim 15, wherein the catalyst is salicylate.

* * * * *